United States Patent
Sim et al.

(10) Patent No.: US 9,895,193 B2
(45) Date of Patent: Feb. 20, 2018

(54) STEERABLE ELECTRODE CATHETER ASSEMBLY

(71) Applicants: Sung Eun Sim, Seoul (KR); Mun Gi Hong, Gyeonggi-do (KR)

(72) Inventors: Sung Eun Sim, Seoul (KR); Mun Gi Hong, Gyeonggi-do (KR)

(*) Notice: Subject to any disclaimer, the term of this patent is extended or adjusted under 35 U.S.C. 154(b) by 388 days.

(21) Appl. No.: 14/334,663

(22) Filed: Jul. 17, 2014

(65) Prior Publication Data

US 2015/0105771 A1 Apr. 16, 2015

(30) Foreign Application Priority Data

Oct. 15, 2013 (KR) .................. 10-2013-0122575

(51) Int. Cl.
*A61B 18/12* (2006.01)
*A61B 18/14* (2006.01)
*A61B 18/00* (2006.01)

(52) U.S. Cl.
CPC .............. *A61B 18/1492* (2013.01); *A61B 2018/00952* (2013.01); *A61B 2018/1475* (2013.01)

(58) Field of Classification Search
CPC ...... A61B 18/1492; A61B 2018/00952; A61B 2018/1475
See application file for complete search history.

(56) References Cited

U.S. PATENT DOCUMENTS

| | | | |
|---|---|---|---|
| 4,790,312 A * | 12/1988 | Capuano, Sr. ... | A61B 17/32001 606/171 |
| 5,304,172 A * | 4/1994 | Manoukian ............ | A61B 18/24 385/60 |
| 5,383,852 A * | 1/1995 | Stevens-Wright ....... | A61M 25/0141 604/95.04 |
| 5,462,527 A * | 10/1995 | Stevens-Wright . | A61B 18/1492 600/585 |
| 5,545,200 A * | 8/1996 | West .................. | A61B 18/1492 606/29 |
| 5,637,090 A * | 6/1997 | McGee ................ | A61B 5/0422 600/374 |
| 6,554,794 B1 * | 4/2003 | Mueller ............. | A61B 17/3478 604/528 |
| 6,602,278 B1 * | 8/2003 | Thompson ........ | A61M 25/0136 604/528 |
| 6,770,070 B1 * | 8/2004 | Balbierz ................ | A61B 10/04 600/566 |
| 2003/0014051 A1* | 1/2003 | Woloszko .......... | A61B 18/1477 606/46 |
| 2004/0087943 A1* | 5/2004 | Dycus ................ | A61B 17/2909 606/51 |
| 2005/0222665 A1* | 10/2005 | Aranyi ................ | A61B 17/068 623/1.11 |
| 2006/0106298 A1* | 5/2006 | Ahmed ................ | A61B 5/0422 600/381 |

(Continued)

*Primary Examiner* — Daniel Fowler
(74) *Attorney, Agent, or Firm* — JCIPRNET

(57) ABSTRACT

Provided is a steerable electrode catheter assembly capable of easily contacting an affected part of a patient when performing an operation on a human body while adjusting a direction of the electrode catheter assembly. In detail, provided is a steerable electrode catheter assembly whereby a length by which a catheter is inserted into an affect part of a patient during an operation on a human body may be easily adjusted and also an angle of a tip portion of the catheter may be easily adjusted by a user.

6 Claims, 6 Drawing Sheets

(56) References Cited

U.S. PATENT DOCUMENTS

2009/0018565 A1\* 1/2009 To .................... A61B 17/32075
606/159
2009/0163915 A1\* 6/2009 Potter ................ A61B 18/1492
606/41

\* cited by examiner

STEERABLE ELECTRODE CATHETER ASSEMBLY

CROSS-REFERENCE TO RELATED APPLICATION

This application claims the priority benefit of Korean patent application serial no. 10-2013-0122575, filed on Oct. 15, 2013. The entirety of the above-mentioned patent application is hereby incorporated by reference herein and made a part of this specification.

BACKGROUND

1. Field

One or more embodiments of the present invention relate to a steerable electrode catheter assembly, and more particularly, to a steerable electrode catheter assembly which is capable of easily contacting an affected part of a patient when performing an operation on a human body while adjusting a direction of the electrode catheter assembly.

2. Description of the Related Art

In general, a medical catheter is inserted into a human body to measure a state of an affected part, cut an affected part or inject medication into an affected part. A catheter is formed of a synthetic resin or a metal and in a pipe form. A user holds a handle of the catheter and inserts a distal end of the catheter into an affected part of a patient to perform an operation.

The above-described catheter may be used in an operation method of selectively blocking spinal nerves by injecting local anesthesia into an epidural part surrounding the spines by inserting an injection pipe. An operation method using a catheter may be used for patients who have pain due to inflammation, adhesion or recurrence after a surgery for a herniated disk, patients with a low back pain or spinal stenosis, patients with a back pain due to neural adhesion, or patients with sciatica.

An operation using the catheter as described above is usually performed by a user by holding a body of the catheter while monitoring an image obtained by using an image capturing unit. As the user has to hold the body of the catheter with a hand and adjust a length of the body of the catheter to be inserted into a body of a patient and also adjust a direction of a distal end tip of the catheter, the operation is difficult. Due to the inconvenient use of the catheter according to the conventional art, time for an operation is prolonged and the inconvenience for the patient is also increased.

SUMMARY

One or more embodiments of the present invention include a steerable electrode catheter assembly whereby a length of a catheter being inserted into an affect part of a patient during an operation on a human body may be easily adjusted and also an angle of a tip portion of the catheter may be easily adjusted by a user.

Additional aspects will be set forth in part in the description which follows and, in part, will be apparent from the description, or may be learned by practice of the presented embodiments.

According to one or more embodiments of the present invention, a steerable electrode catheter assembly includes: a housing formed to be manipulated by a user by holding the housing with a hand, wherein the housing includes an upper body and a lower body which are separated from each other, and a hollow portion is formed between the upper body and the lower body; an external member that has a pipe form and is slidably mounted to move in forward and backward directions with respect to the housing; a catheter that is mounted between the upper body and the lower body of the housing while a tip portion of the catheter which is a distal end portion is developed to the distal direction and a proximal end portion of the catheter is inserted into the external member, wherein the catheter includes a tip electrode mounted at the tip portion, which is the distal end portion, a ring electrode, and a pair of wires respectively connected to the tip electrode and the ring electrode; a position adjusting member that is mounted to the housing to move the external member forward or backward with respect to the catheter and the housing to thereby adjust a position of the external member; and a direction adjusting member that is mounted to the housing to pull at least one of the pair of the wires of the catheter.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
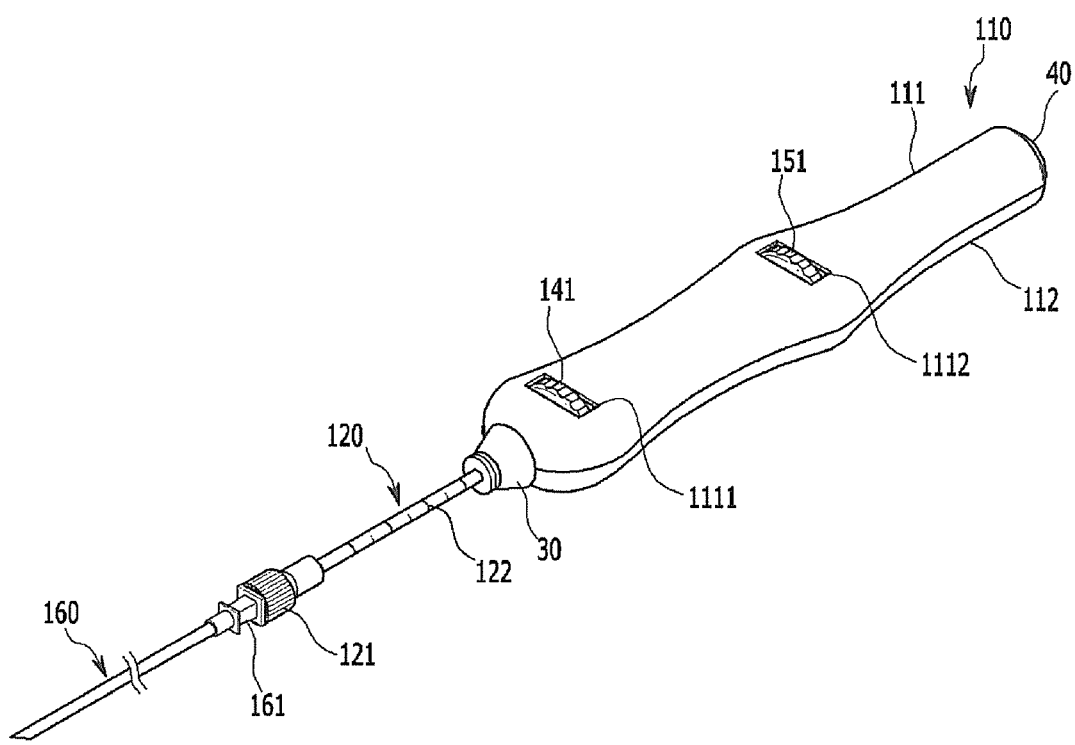
FIG. 1 is a perspective view of a steerable electrode catheter assembly according to an embodiment of the present invention.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

Figure 2:
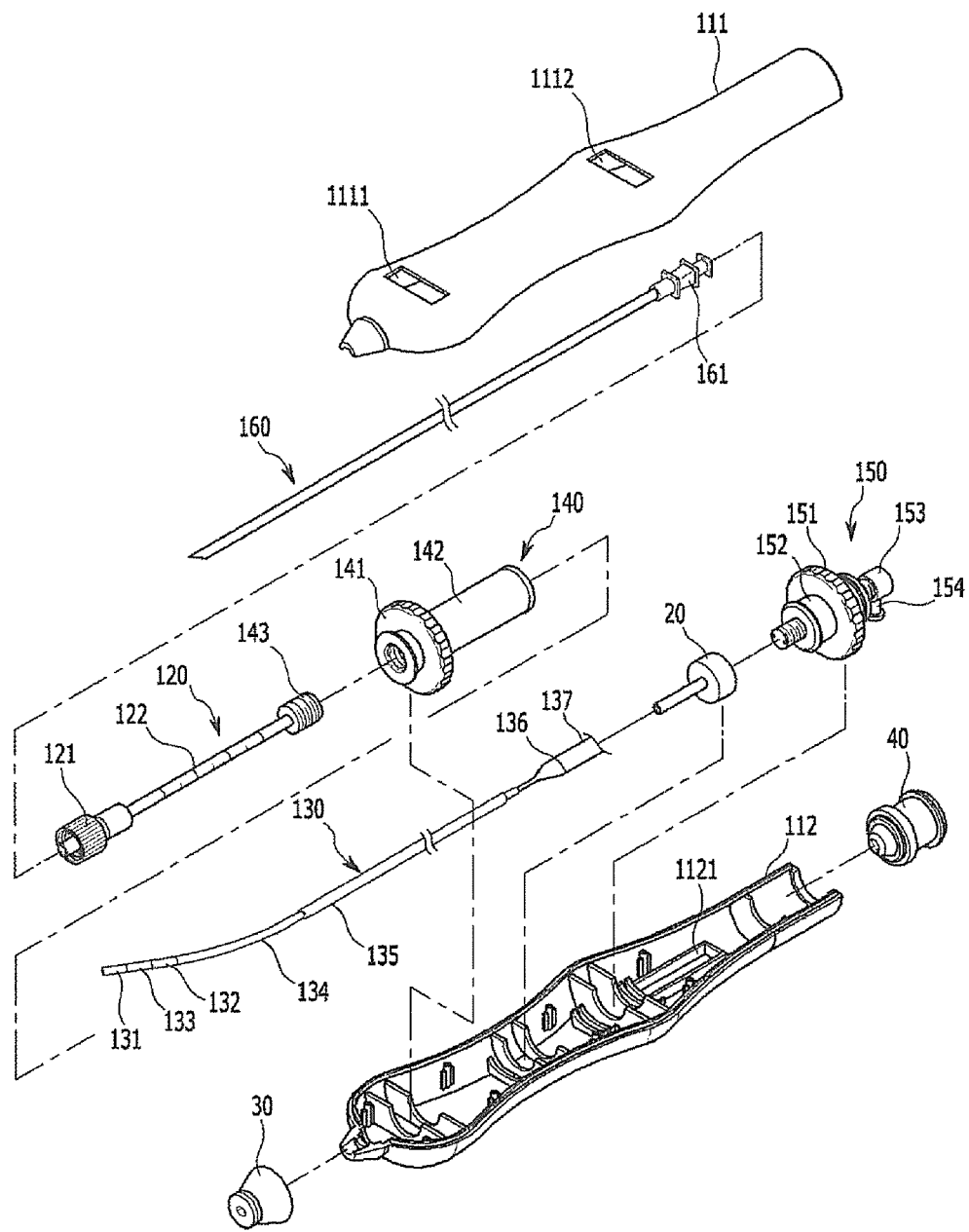
FIG. 2 is a disassembled perspective view of the steerable electrode catheter assembly of FIG. 1.
Figure 3:
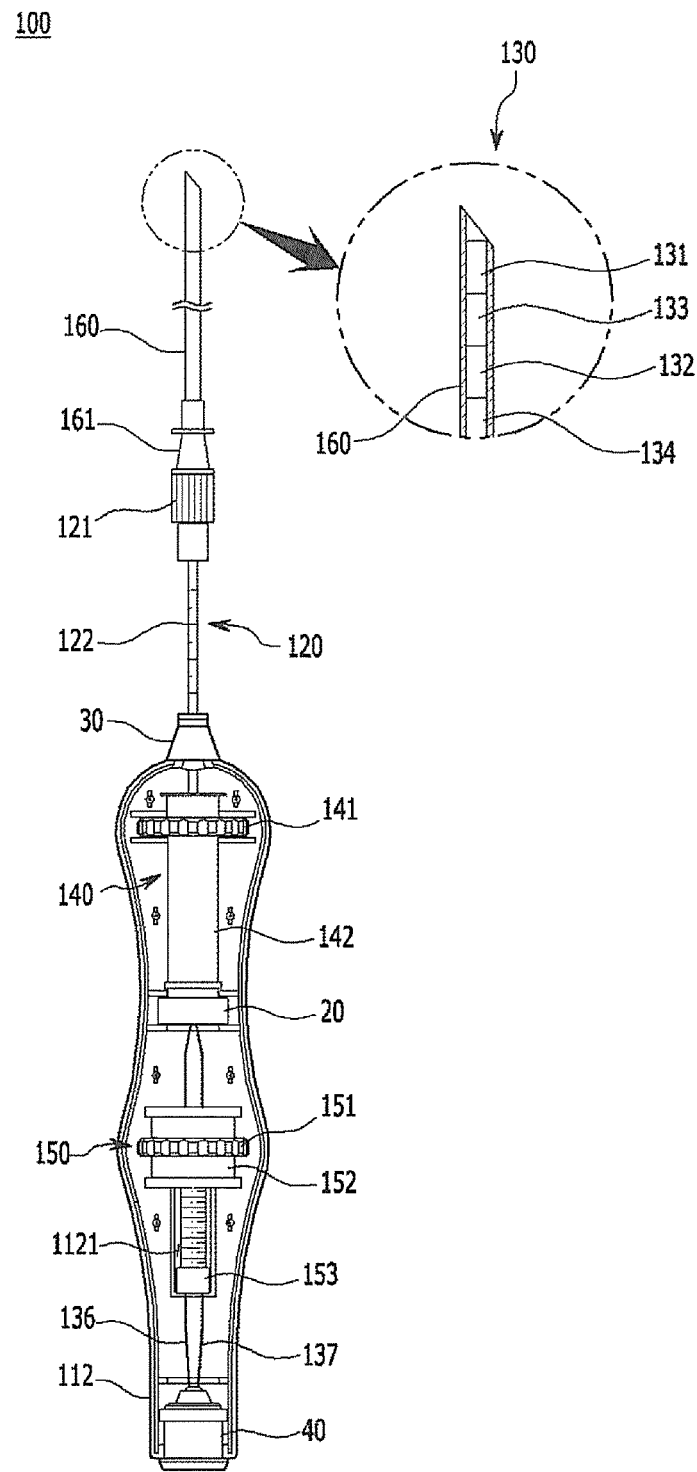
FIG. 3 is a plan view of the steerable electrode catheter assembly of FIG. 1 with an opened upper portion.

FIG. 1 is a perspective view of a steerable electrode catheter assembly 100 according to an embodiment of the present invention. FIG. 2 is a disassembled perspective view of the steerable electrode catheter assembly 100 of FIG. 1. FIG. 3 is a plan view of the steerable electrode catheter assembly 100 of FIG. 1 with an opened upper portion.

Referring to FIGS. 1 through 3, the steerable electrode catheter assembly 100 includes a housing 110, an external member 120, a catheter 130, a position adjusting member 140, a direction adjusting member 150, and an guide pipe 160.

The housing 110 includes an upper body 111 and a lower body 112 that are horizontally separated from each other. The housing 110 may be manipulated by a user by holding with a hand. A hollow portion is included between the upper body 111 and the lower body 112 of the housing 110. A first through hole 1111 and a second through hole 1112 are formed in the housing 110. The first through hole 1111 and the second through hole 1112 are formed in each of the upper body 111 and the lower body 112.

The position adjusting member 140 includes a position adjusting dial 141 and a position adjusting body 142. The position adjusting body 142 is cylindrical and is rotatably mounted inside the housing 110. The position adjusting dial 141 is coupled to the position adjusting body 142. The position adjusting dial 141 is mounted such that a portion thereof protrudes out of the housing 110 through the first through hole 1111. The user manipulates the position adjusting member 140 by rotating the position adjusting dial 141 with a finger. A female screw portion is formed in the position adjusting body 142.

The external member 120 is formed in a pipe form. An external diameter of a cross-section of the external member 120 may be non-circular. An external diameter of a cross-section of the external member 120 of the steerable electrode catheter assembly according to the present embodiment is oval. The external member 120 is slidably mounted in the housing 110 to move in forward and backward directions with respect to the housing 110. A portion of the housing 110 supporting an external diameter of the external member 120 has a shape corresponding to the non-circular shape of the external diameter of the external member 120. Thus, the housing 110 slidably supports the external member 120 in a longitudinal direction and prevents rotation of the external member 120 at the same time.

A proximal end portion of the catheter 130 is inserted into the external member 120. The external member 120 includes a first coupling portion 121 disposed at a distal end portion thereof. A female screw portion is formed in the first coupling portion 121 so as to be coupled to the guide pipe 160. Dimensions 122 are marked on an external surface of the external member 120.

A movable screw portion 143 is coupled to a proximal end portion of the external member 120. A male screw portion is formed on the movable screw portion 143. The movable screw portion 143 is screw-coupled to the female screw portion formed in the position adjusting body 142. As described above, as the housing 110 prevents rotation of the external member 120 and slidably supports the external member 120 in a longitudinal direction, when the position adjusting dial 141 is rotated, the external member 120 moves forward or backward via an operation of the movable screw portion 143. The position adjusting dial 141 includes an uneven portion on an external surface thereof so as to turn the same while holding the housing 110 with a hand.

The catheter 130 includes a tip electrode 131, a ring electrode 132, an insulator 133, a tube 134, a rigid pipe 135, a first wire 136, and a second wire 137.

The tip electrode 131 is mounted at a distal end portion of the catheter 130. The first wire 136 is coupled to the tip electrode 131 to extend in a longitudinal direction.

The ring electrode 132 is ring-shaped and is mounted at the proximal position of the tip electrode 131. The second wire 137 is coupled to the ring electrode 132 to extend in a longitudinal direction.

Power is supplied from the outside through the first wire 136 and the second wire 137 to thereby supply power to the tip electrode 131 and the ring electrode 132, respectively. An external surface of one of the first and second wires 136 and 137 or both external surfaces of the first and second wires 136 and 137 are coated with an insulating layer so as to prevent electric conduction between the first and second wires 136 and 137.

The insulator 133 is disposed between the tip electrode 131 and the ring electrode 132. The insulator 133 electrically insulates the tip electrode 131 and the ring electrode 132 from each other.

The tube 134 is connected to the ring electrode 132. The tube 134 is formed of an elastic insulating material. A tension applied to the first wire 136 is transmitted to the tube 134 so as to bend the tube 134, thereby adjusting directions of the tip electrode 131 and the ring electrode 132.

A proximal portion of the tube 134 is inserted into the rigid pipe 135 to be supported. The rigid pipe 135 receives the tension applied to the first wire 136 to thereby support the tube 134 such that the tube 134 may be elastically deformed. The rigid pipe 135 is mounted between the upper body 111 and the lower body 112, while being inserted into the external member 120. The rigid pipe 135 is fixed in the housing 110 by using a supporting body 20 as illustrated in FIG. 2. The supporting body 20 is coupled to the rigid pipe 135 to be firmly fixed to the housing 110, thereby supporting the rigid pipe 135 such that the rigid pipe 135 does not shake or rotate.

The first wire 136 is connected to the direction adjusting member 150 and pulled in this state, thereby adjusting the direction of the tip electrode 131.

The direction adjusting member 150 includes a direction adjusting dial 151, a dial body 152, an operation screw portion 153, and a mounting bolt 154.

The direction adjusting dial 151 is mounted to the housing 110 such that a portion of the direction adjusting dial 151 protrudes out of the housing 110 through the second through hole 1112. The direction adjusting dial 151 includes an uneven portion on an external surface thereof so that the user may easily rotate the same with a finger.

The dial body 152 is rotatably mounted to the housing 110. The dial body 152 is cylindrical and includes a female screw portion on an inner surface thereof. The direction adjusting dial 151 is coupled to the dial body 152.

The operation screw portion 153 includes a male screw portion on an external surface thereof so as to be screw-coupled to the female screw portion formed in the dial body 152. A through hole formed in a longitudinal direction is formed in the operation screw portion 153, and the first wire 136 and the second wire 137 are disposed to pass through the through hole of the operation screw portion 153. The mounting bolt 154 is coupled to the operation screw portion 153. The mounting bolt 154 is slidably inserted into a guide groove portion 1121 formed on a lower surface of the lower body 112 to extend in a longitudinal direction. As the direction adjusting dial 151 rotates, the mounting bolt 154 is caught by the guide groove portion 1121 so that the operation screw portion 153 does not rotate but the operation screw portion 153 and the mounting bolt 154 move forward and backward. The first wire 136 is fixed at a position by being wound around the operation screw portion 153. When the operation screw portion 153 moves forward or backward, the first wire 136 is unwound or pulled.

When the operation screw portion 153 moves backward to pull the first wire 136, the tube 134 is bent to thereby adjust the directions of the tip electrode 131 and the ring electrode 132 of the catheter 130.

The guide pipe 160 is in the form of a pipe through which the catheter 130 may be inserted and an end portion of the guide pipe 160 is sharply formed. The guide pipe 160 supports the catheter 130 to thereby guide insertion of the catheter 130 into the body of a patient. The guide pipe 160 includes a second coupling portion 161. The second coupling portion 161 is disposed at a proximal end portion of the guide pipe 160. The second coupling portion 161 is screw-coupled to the first coupling portion 121 of the external member 120 as illustrated in FIG. 3 to thereby couple the guide pipe 160 and the external member 120.

The housing 110 includes a distal cover 30 and a proximal cover 40. The distal cover 30 is disposed in distal end of the housing 110 to support the catheter 130 and the external member 120. In particular, as the distal cover 30 having a shape corresponding to the oval external cross-section of the external member 120 described above supports the external member 120, sliding of the external member 120 in a longitudinal direction is allowed but rotation of the external member 120 is prevented.

The proximal cover 40 is disposed at the proximal part of the housing 110. An electrode terminal through which the steerable electrode catheter assembly 100 is to be connected to an external power supply is included in the proximal cover 40, and the first wire 136 and the second wire 137 are electrically connected to the electrode terminal.

Figure 4:
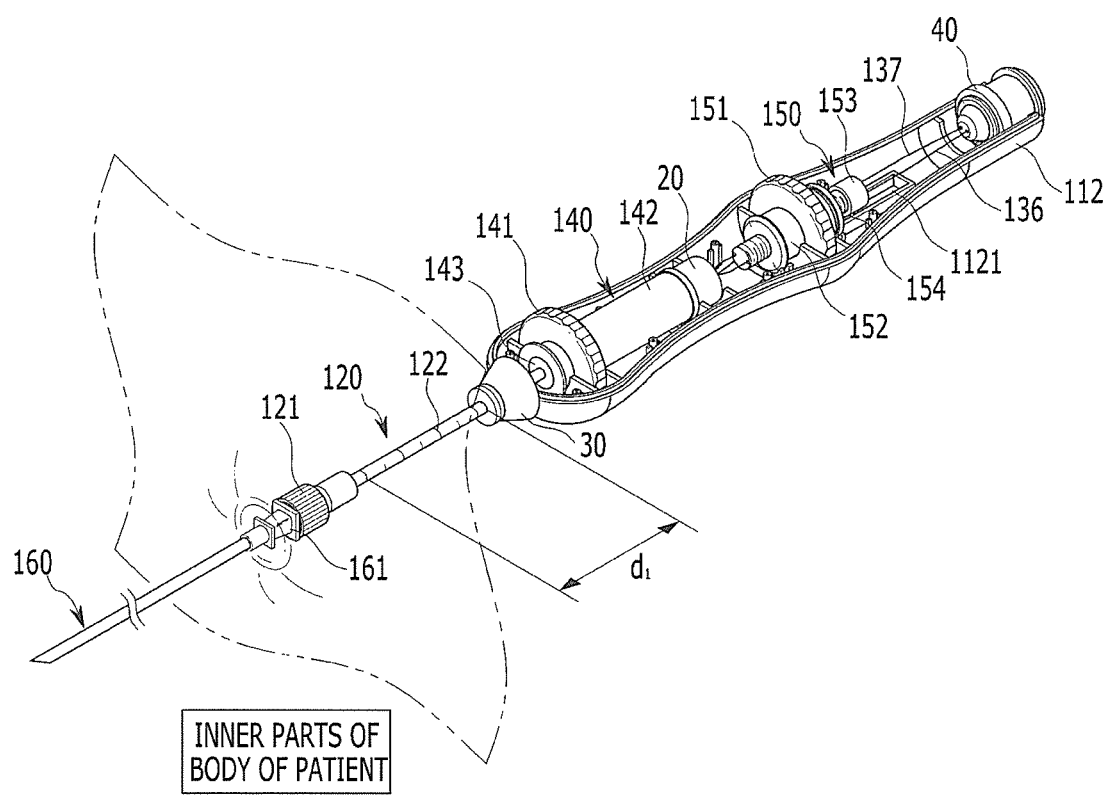
FIGS. 4 through 6 are operational diagrams illustrating an operation of the steerable electrode catheter assembly of FIG. 1.
Figure 5:
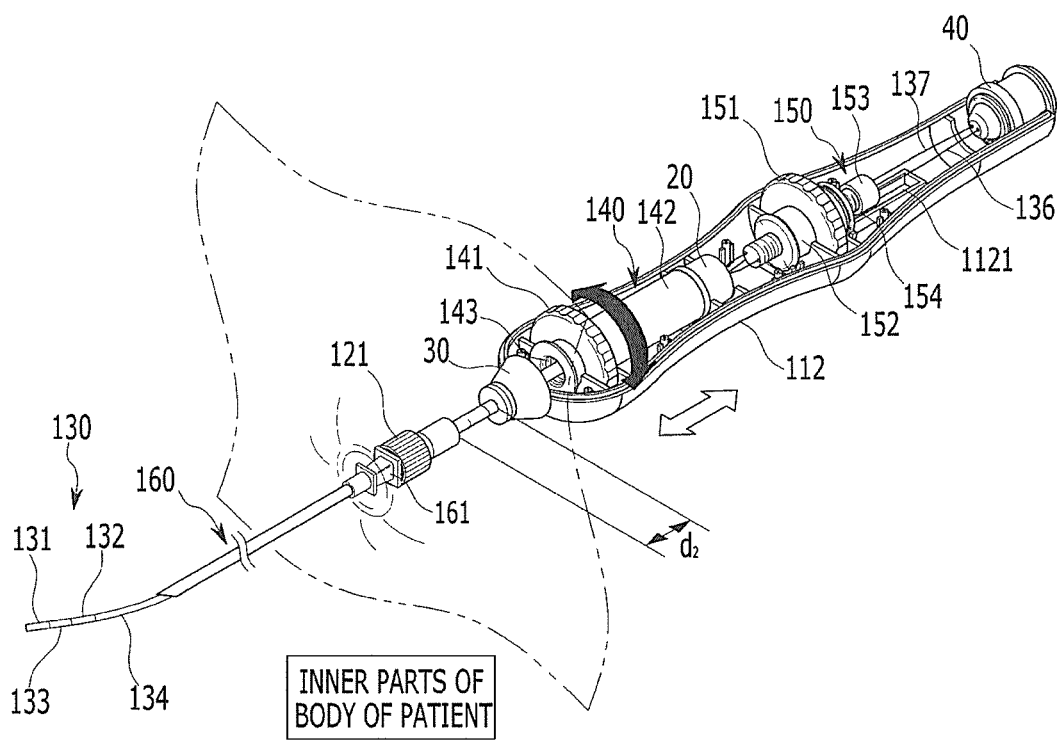
Figure 6:
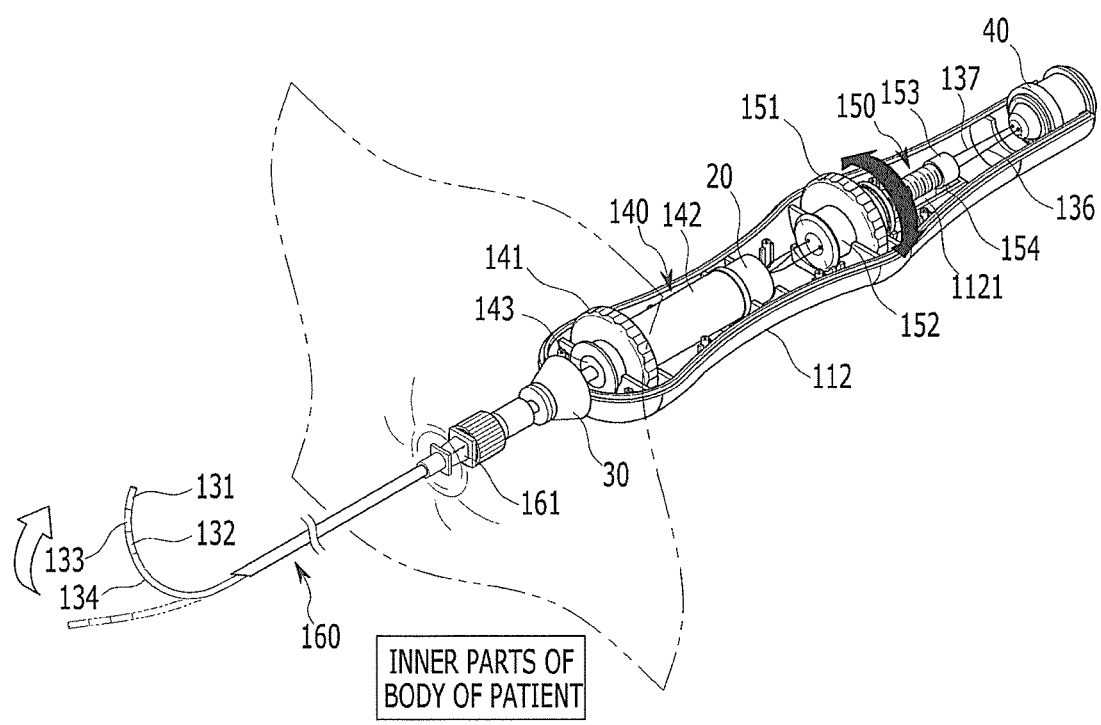

Hereinafter, an operation of the steerable electrode catheter assembly 100 having the above-described structure will be described. FIGS. 4 through 6 are operational views illustrating an operation of the steerable electrode catheter assembly 100 of FIG. 1.

The steerable electrode catheter assembly 100 according to the present embodiment is typically used by coupling the guide pipe 160 and the catheter 130 as illustrated in FIG. 1. Before coupling the guide pipe 160 and the catheter 130 as described above, the guide pipe 160 is first inserted into the body of a patient. The guide pipe 160 having a thin and long needle inserted into an inner diameter portion thereof is inserted into the body of the patient. In this state, the thin and long needle is removed from the guide pipe 160, and the catheter 130 is inserted into the guide pipe 160 as illustrated in FIG. 1. When the catheter 130 is inserted into the guide pipe 160, the tip electrode 131 and the ring electrode 132 of the catheter 130 protrude through an end portion of the guide pipe 160 so as to be located in the body of the patient.

By screw-coupling the second coupling portion 161 of the guide pipe 160 and the first coupling portion 121 of the external member 120 in this state, the guide pipe 160 is fixed to the external member 120.

As illustrated in FIG. 4, while the external member 120 is moved forward, the end portion of the catheter 130 is located inside the guide pipe 160. Here, a length d1 by which the external member 120 is moved forward may be confirmed through the dimensions 122 displayed on the external member 120.

By rotating the position adjusting dial 141 of the position adjusting member 140 in a direction in this state, the movable screw portion 143 of the position adjusting member 140 moves backward. Here, the external member 120 coupled to the movable screw portion 143 also moves backward along with the movable screw portion 143. When the external member 120 moves backward, the guide pipe 160 also moves backward, and as a result, the end portion of the catheter 130 moves forward with respect to the guide pipe 160. Due to this relative movement between the guide pipe 160 and the catheter 130, the catheter 130 moves forward inside the body of the patient as illustrated in FIG. 5. A length by which the catheter 130 has moved forward in the body of the patient may be easily detected by the user based on a difference between the length d1 of the external member 120 illustrated in FIG. 4 and a length d2 of the external member 120 illustrated in FIG. 5. By using the dimensions 122 displayed on the external member 120 as above, the length by which the catheter 130 protrudes in the body of the patient may be easily detected without using a radiation imaging apparatus.

Next, an operation of adjusting a direction of the catheter 130 will be described. When the direction adjusting dial 151 of the direction adjusting member 150 is rotated in a direction, the operation screw portion 153 moves backward with respect to the dial body 152. Here, the first wire 136 fixed to the mounting bolt 154 also moves backward, and as a result, the tip electrode 131 is pulled. The tube 134 that has received the tension of the first wire 136 through the tip electrode 131 is elastically deformed to be bent as illustrated in FIG. 6. When the direction adjusting dial 151 is rotated in an opposite direction, the first wire 136 is unwound to stretch the tube 134. Thus, the directions of the tip electrode 131 and the ring electrode 132 of the catheter 130 may be easily adjusted by rotating the direction adjusting dial 151.

When the tip electrode 131 and the ring electrode 132 are brought into contact with an affected part, on which an operation is to be performed, after adjusting a length and a direction of the catheter 130, power is supplied to the tip electrode 131 and the ring electrode 132 to perform an operation on the affected part.

As described above, according to the steerable electrode catheter assembly 100, a length of the catheter 130 inserted into the human body may be easily adjusted and a tip portion which is a distal end portion of the catheter 130 that contacts the affected part may be easily bent in an angle desired by a user. Thus, user convenience is increased. Consequently, for example, an operation time may be reduced, which results in reducing the pain of the patient.

While the steerable electrode catheter assembly according to the present invention has been particularly shown and described with reference to exemplary embodiments thereof, the scope of the invention is not limited to the embodiments set forth and illustrated herein.

For example, while the first coupling portion 121 of the external member 120 and the second coupling portion 161 of the guide pipe 160 that are screw-coupled are described above, they may also be detachably coupled to each other by insertion. That is, one of the first and second coupling portions 121 and 161 may include a protrusion and the other may include a groove portion corresponding to the protrusion so that they may be detachably coupled to each other by insertion.

Also, while the guide pipe 160 formed of a metal is described above, as long as easy insertion into the human body is allowed, the guide pipe 160 may be formed of other various materials.

Also, while only the first wire 136 that is fixed to the mounting bolt 154 to be pulled is described above, according to circumstances, the second wire 137 may also be fixed to the mounting bolt 154 to be pulled.

In addition, while the external member 120 has a pipe form having an oval cross-section, the external member 120 may also have other various non-circular cross-sections. According to circumstances, forward and backward movement of the external member 120 may adjusted to some extent even when a cross-section thereof is circular.

As described above, according to the one or more of the above embodiments of the present invention, the steerable electrode catheter assembly having a simple structure that is easy to use is provided.

Also, according to the steerable electrode catheter assembly of the embodiments of the present invention, a length by which a catheter is inserted into the human body may be easily adjusted, and an angle of the tip portion of the catheter which is a distal end portion that contacts an affected part may be easily adjusted in a direction desired by a user.

Also, according to the steerable electrode catheter assembly of the embodiments of the present invention, the length by which the catheter is inserted into the human body may be easily detected and adjusted also from the outside of skin.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A steerable electrode catheter assembly, comprising:
   a housing formed to be manipulated by a user by holding the housing with a hand, wherein the housing includes an upper body and a lower body which are separated from each other, and a hollow portion is formed between the upper body and the lower body;
   an external member that has a pipe form and is slidably mounted in the housing to move in forward and backward directions with respect to the housing, wherein the housing supports the external member by surrounding an external surface of the external member according to a non-circular external diameter of the external member so as to allow sliding of the external member in a longitudinal direction and prevent rotation of the external member;
   a catheter that is mounted between the upper body and the lower body of the housing while a tip portion of the catheter which is a distal end portion is extended to the distal direction and a proximal end portion of the catheter is inserted into the external member, wherein the catheter includes a tip electrode mounted at the tip portion, which is the distal end portion, a ring electrode, and a pair of wires respectively connected to the tip electrode and the ring electrode;
   an guide pipe, detachably coupled to the external member, wherein dimensions are displayed on an external surface of the external member in order to allow to detect a relative position of the catheter with respect to the guide pipe while the catheter and the guide pipe are inserted into a human body;
   a position adjusting member that is mounted to the housing to move the external member forward or backward with respect to the catheter and the housing to thereby adjust a position of the external member, wherein the position adjusting member comprises:
      a position adjusting dial mounted to the housing such that a portion of the position adjusting dial protrudes outside through a through hole formed in the housing;
      a position adjusting body that is cylindrical and includes a female screw portion on an inner portion and is coupled to the position adjusting dial; and
      a male screw portion that is mounted to the external member and is screw-coupled to the female screw portion formed in the position adjusting body so as to move forward or backward via rotation of the position adjusting dial, wherein the external member moves forward or backward along with the male screw portion; and
   a direction adjusting member that is mounted to the housing to pull at least one of the pair of the wires of the catheter.

2. The steerable electrode catheter assembly of claim 1, wherein the tip electrode and the ring electrode of the catheter are formed of a metal, and a bending section between the tip electrode and the ring electrode and a bending section between the ring electrode and the catheter are formed of an insulator.

3. The steerable electrode catheter assembly of claim 1, the guide pipe that is cylindrical so as to support and guide the catheter when inserting the catheter into the human body so that the catheter is inserted into the guide pipe.

4. The steerable electrode catheter assembly of claim 3, wherein the external member comprises a first coupling portion formed at a distal end portion, and the guide pipe comprises a second coupling portion formed at a proximal end portion, and
   wherein the external member and the guide pipe are detachably coupled to each other via screw-coupling between the first coupling portion and the second coupling portion.

5. The steerable electrode catheter assembly of claim 1, wherein the direction adjusting member comprises:
   a direction adjusting dial mounted to the housing such that a portion of the direction adjusting dial protrudes outside through a through hole formed in the housing;
   a dial body that is cylindrical and includes a screw thread on an inner portion and is coupled to the direction adjusting dial;
   an operation screw portion that is coupled to at least one of the pair of the wires and is screw-coupled to the dial body so as to move forward or backward via rotation of the direction adjusting dial; and
   a mounting bolt that is coupled to a lower end of the operation screw portion to prevent rotation of the operation screw portion and is slidably mounted to the lower body to move in forward and backward directions.

6. The steerable electrode catheter assembly of claim 1, wherein the external diameter of the cross-section of the external member is oval.

* * * * *